United States Patent [19]

Eichel et al.

[11] Patent Number: 5,102,668

[45] Date of Patent: * Apr. 7, 1992

[54] SUSTAINED RELEASE PHARMACEUTICAL PREPARATION USING DIFFUSION BARRIERS WHOSE PERMEABILITIES CHANGE IN RESPONSE TO CHANGING PH

[75] Inventors: Herman J. Eichel; Brent D. Massmann, both of Columbus, Ohio

[73] Assignee: Kingsform Technology, Inc., Dayton, Ohio

[ * ] Notice: The portion of the term of this patent subsequent to Jan. 8, 2008 has been disclaimed.

[21] Appl. No.: 593,768

[22] Filed: Oct. 5, 1990

[51] Int. Cl.⁵ .................... A61K 9/16; A61K 9/52; A61K 9/54

[52] U.S. Cl. .................... 424/490; 424/458; 424/459; 424/461; 424/462; 424/473; 424/494; 424/497

[58] Field of Search .................... 424/490, 489, 494

[56] References Cited

U.S. PATENT DOCUMENTS

| | | | |
|---|---|---|---|
| 4,205,060 | 5/1980 | Monsimer et al. | 424/14 |
| 4,734,285 | 3/1988 | Alderman | 424/468 |
| 4,752,470 | 6/1988 | Mehta | 424/459 |
| 4,772,475 | 9/1988 | Fukui et al. | 424/468 |
| 4,816,264 | 3/1989 | Phillips et al. | 424/468 |
| 4,876,097 | 10/1989 | Autant et al. | 424/438 |
| 4,917,900 | 4/1990 | Jones et al. | 424/490 |
| 4,925,676 | 5/1990 | Ghebre-Sellassie et al. | 424/470 |
| 4,927,639 | 5/1990 | Ghebre-Sellassie et al. | 424/497 |
| 4,927,640 | 5/1990 | Dahlinder et al. | 424/494 |
| 4,983,401 | 1/1991 | Eichel et al. | 424/490 |

*Primary Examiner*—Thurman K. Page
*Assistant Examiner*—James M. Spear
*Attorney, Agent, or Firm*—Killworth Gottman Hagan & Schaeff

[57] ABSTRACT

A sustained-release pH independent pharmaceutical preparation having multi-units of microparticles comprising a granular drug which is less soluble at low pH and more soluble at high pH. The granular drug is surrounded by or admixed with a pH controlled material formed from at least one polymer that is hydrophilic at low pH and hydrophobic at higher pH and is in a ratio with the granular drug such that the resulting sustained-release pharmaceutical preparation is independent from the pH environment. The resulting sustained-release pH independent pharmaceutical preparation allows a uniform release of drug for a period of at least 12 to 24 hours. In an alternative embodiment, the drug may be more soluble at low pH and less soluble at higher pH and the pH controlled material formed from at least one polymer that is hydrophobic at low pH and hydrophilic at higher pH.

16 Claims, No Drawings

SUSTAINED RELEASE PHARMACEUTICAL PREPARATION USING DIFFUSION BARRIERS WHOSE PERMEABILITIES CHANGE IN RESPONSE TO CHANGING PH

BACKGROUND OF THE INVENTION

The present invention relates to oral sustained release pharmaceutical preparations in the form of microparticles of granular drug, a pH controlled material, and a diffusion membrane. More particularly, the present invention relates to using PH controlled material to produce a formulation having a sustained release of drug whereby the release is independent of the pH environment.

As is well known, the maximum time of effectiveness in many pharmaceutical preparations, particularly those containing a drug such as gemfibrozil, ibuprofen, indomethacin, and naproxen, etc. is only a few hours because of biological modification and/or elimination of the medication in the body. Consequently, repeated dosages must be taken at frequent intervals to obtain long term therapeutic levels of drug. Furthermore, these drugs usually dissolve readily in the digestive juices and the total dosage is immediately fed into the blood stream. After high initial peak concentrations, the level of drug in the blood stream constantly decreases because of the biological elimination, so there is little or no therapeutic effect at the end of the period between dosages. As a result, the therapeutic effect fluctuates between dosages corresponding to the peaks and valleys in the level of drug in the blood as commonly measured by trough to peak ratios. Many attempts have been made to control the release of the medication to minimize the trough to peak ratios.

However, most conventional sustained-release formulations of drugs which contain acid and/or amine functionalities have a release rate that is strongly dependent on pH. Since the pH of the human gastro-intestinal tract ranges from about 1 to 7.5 in a variable manner, the drug release is erratic. In addition, conventional sustained release formulations of drugs that contain acid or amine functionalities are poorly bioavailable when local gastro-intestinal pH causes the drug to be poorly soluble. Furthermore, conventional formulations such as these risk the rapid release or dumping of drugs when local gastro-intestinal pH causes excessively rapid drug dissolution. Consequently, a sustained and uniform release of drug for a period of at least 12 to 24 hours has not previously been possible.

Still, it has been known that various polymers can be used with the drug core and further, it has been known that a control coat can be formed over this core. For example, Mousimer et al in U.S. Pat. No. 4,205,060 forms a microcapsule comprising a core containing a water soluble salt of a medicament and a polymer, e.g. the salt of a medicament containing an amino-group and a carboxyl group containing polymer, and a sheath of a water-insoluble film forming polymer e.g. ethyl cellulose. Likewise, Fukui et al in U.S. Pat. No. 4,772,475 discloses a pharmaceutical controlled-release individual units or multiple units formulation comprising a granulation product of a drug and a release controlling agent such as acrylic acid polymers, acrylic acid copolymers and mixtures thereof with cellulose derivatives and crystalline cellulose, with a sheath formed by conventional encapsulation. See also, Phillips et al, U.S. Pat. No. 4,816,264 which discloses a drug core containing a hydrocolloid gelling polymer such as hydroxyethyl cellulose and an Eudragit E-30-D sheath. However, when used for drugs with acid or amine functionalities all of these use conventional sustained release formulations which are not pH independent and thus, have the aforementioned non-uniform drug release problems.

Thus, there remains a need for a pharmaceutical preparation that releases drug independent from the pH of the environment and therefore, is capable of providing a uniform and sustained release of drug for a period of at least 12 to 24 hours.

SUMMARY OF THE INVENTION

The present invention meets the aforementioned need by providing a sustained-release pH independent pharmaceutical preparation having a uniform and sustained release of drug for at least 12 to 24 hours.

In one form of the present invention, the pharmaceutical preparation contains multi-units of microparticles comprising a granular drug that is less soluble at low pH and more soluble at high pH. The granular drug is admixed with or surrounded by a pH controlled material which is formed from at least one polymer that is hydrophilic at low pH and hydrophobic at higher pH. The pH controlled material is in a ratio with the granular drug such that the resulting sustained release pharmaceutical preparation is independent of the pH environment.

In this embodiment, the granular drug may include, but it not limited to, ibuprofen, gemfibrozil, indomethacin, Clinoril TM (sulindac), naproxen, tolmetin, fenoprofen, or furosemide. The granular drug may be admixed with the pH controlled material, such as by extrusion of the drug with the polymer and, then, spheronizing or the spherical core may be formed by wet granulation. The resulting spheroidal core preferably has a size range from about 100 to 2000 microns. Polymers which are pH controlled and may use as the pH controlled material include Eudragit E100 (an acrylic resin with tertiary amine side chains from Rohm Pharma), other tertiary amine derivatives of polyacrylates, polymethacrylates, polyvinyl derivatives, and cellulose derivatives (cellulosics). These pH controlled polymers may be blended with other excipients. The ratio of the pH controlled material to granular drug is preferably less than 1:2 but greater than 1:50. A diffusion membrane may, then, be coated over the spherical core. Preferably the diffusion membrane is a pH neutral polymer such as Eudragit NE30D acrylic resin (Rohm Pharma) or Aquacoat ethylcellulose emulsion (FMC).

Alternatively, the pH controlled material may be admixed into the diffusion membrane which is applied as a layer over the granular drug or may be layered onto the granular drug followed by a diffusion membrane layer. In either event the layers may be applied by a spray coating process.

In another embodiment of the present invention, the sustained-release pH independent pharmaceutical preparation may be comprised of a granular drug which is more soluble low pH and less soluble at high pH. The pH controlled material in this instance is formed from at least one polymer which is hydrophobic at low pH and hydrophilic at higher pH. As in the first embodiment, the pH controlled material is in a ratio with the granular drug such that the resulting sustained-release pharmaceutical preparation is independent of the pH environment.

The drug choice of the alternate pharmaceutical preparation includes dipyridamole, verapamil, chlorpheniramine, pseudoephedrine, quinidine, and clonidine. In this embodiment the polymer used as the pH controlled material may be that disclosed in copending application Ser. No. 354,105, filed May 22, 1989, now U.S. Pat. No. 4,983,401, issued Jan. 8, 1991, the disclosure of which is hereby incorporated by reference. As disclosed there, the preferred polymer is cellulose acetate phthalate (CAP) which has been modified to render it insoluble at intestinal pH, or an insoluble diffusion barrier such as a methacylic/acrylic acid ester copolymer (MAA) which has been modified to render it pH sensitive. In addition to these polymers, cellulose acetate trimellitate, hydroxyethyl cellulose phthalate, cellulose acetate tetrahydrophthalate, hydroxypropylmethyl cellulose phthalate and polyvinyl acetate phthalate may be modified by attachment of hydrophobic side chains such as long chain fatty acids so that they form films with low permeability in acidic environments but remain intact but have higher permeability at alkaline or neutral pH.

Alternatively, enteric polymers may be admixed with polymers that form neutral diffusion membranes to form matrices or diffusion membrane coatings with permeabilities that increase with increasing pH. Similar to the aforementioned pharmaceutical preparation, it is preferred that the ratio of pH controlled material to the granular drug is less than 1:2 but greater than 1:50. Also, the preparation may include a pH neutral coat and/or another coat of the aforementioned pH controlled polymer. An enteric polymer outer sheath may also be used to give a delayed release of drug. Finally, it is preferred that the granular core of drug comprise spherical microparticles having a size range from about 100 to 2000 microns.

Accordingly, it is an object of the present invention to provide a sustained-release pH independent pharmaceutical preparation which allows for a uniform release of drug independent from the pH environment and is capable of providing a release of drug for a period of at least 12 to 24 hours. It is also an object of the present invention to provide a drug that has an high adsorption rate in the intestinal tract without rapidly or erratically dumping excessive amounts of drug thus resulting in a sustained and uniform release of drug.

These and other objects, features and attendant advantages of the present invention will become apparent to those skilled in the art from a reading of the following detailed description of the preferred embodiment and the appended claims.

DETAILED DESCRIPTION OF THE PREFERRED EMBODIMENTS

In one embodiment of the present invention, the preferred sustained-release pH independent pharmaceutical preparation includes the granular drug such as ibuprofen and a relatively thin membrane or matrix of polymer such as Eudragit E100 (Rohm Pharma) as the pH controlled material, together in microparticle form. With this embodiment, the drug has an acid functionality which is the only hydrophilic portion of the molecules and therefore, the solubility varies widely over the gastro-intestinal pH range. When the solubility of the drug increases with increasing pH, as does ibuprofen, the pH controlled material must have the opposite characteristic so as to counteract the drug's permeability thus producing a formulation that is pH independent.

More particularly, the drug should be hydrophobic at low pH and hydrophilic at high pH while the pH controlled material is hydrophilic at low pH and hydrophobic at high pH. Examples of polymers that can be used as the pH controlled material include Eudragit E100, tertiary amine derivatives of polyacrylates, polymethacrylates, polyvinyl derivatives (polyvinyls), and cellulose derivatives (cellulosics). The preferable ratio of the pH controlled material with the granular drug is gauged so that the dissolution rate of the resulting microparticles is not affected by the pH of the environment, namely, the gastro-intestinal tract. The preferable ratio of pH controlled material with granular drug is 1:20 to 1:4. The pH controlled material is preferably the polymer Eudragit E100, but can also be any polymer that is hydrophilic at low pH and Hydrophobic at high pH so long as the polymer is non-toxic. These polymers form membranes which have permeabilities that decrease with increasing pH.

It is preferable that the chosen pH controlled material forms a diffusion barrier for the drug and has pH dependency such that the permeability decreases with increasing pH. Preferably, the aforementioned polymers which have permeabilities that decrease with increasing pH are used in sustained-release formulations having drugs which have solubility rates which increase with increasing pH thus providing release rates which are practically pH independent. The polymers may be used with other excipients to form matrices or coatings. Preferably, the matrices are formed as microparticles by extrusion of the drug with the polymer and then spheronized so as to have a size range from about 100 to 2000 microns.

The resulting microparticles may further be coated with a diffusion membrane to act in concert with the pH controlled material to provide a more controlled release. The diffusion membrane may be a neutral coat such as Eudragit NE30D acrylic resin (Rohm Pharma) or Aquacoat ethylcellulose emulsion (FMC), or another coat of the aforementioned pH controlled material, or mixtures thereof.

The diffusion membrane is preferably formed by spray coating. Likewise, the pH controlled material when applied as a layer, alone or in combination with other coating materials as discussed above, may be spray coated onto the granular drug. The polymer may be sprayed from an aqueous or organic solution or a latex emulsion. When a spherical core is used, it may be the drug and polymer extrudate, drug layered onto non-pareils, particles of pure drug, or wet granulated particles of drug and polymer preferably formed by the Wurster or Tangential Spray Rotor processes. Furthermore, the polymer may be admixed with neutral film forming polymers such as Eudragit NE30D (Rohm Pharma) or Aquacoat to form matrices with a wide range of permeabilities and pH dependencies. Also, plasticizers and other excipients may be used in the spray formulation.

The following examples further illustrate and define this embodiment of the present invention.

EXAMPLE I

Ibuprofen Microparticles

Since the solubility of ibuprofen increases with increasing pH, the drug was mixed with Eudragit E100 and extruded to form microparticles with a membrane that impedes dissolution more at higher pH than at lower pH. 53.1 grams of E100 were dissolved in a solution prepared by adding 16 g concentrated HCl to 160 ml of water. The polymer solution was slowly added to 900 g of powdered ibuprofen in a 20 quart mixer (Hobart model A200). The polymer solution and drug were thoroughly mixed to form an extrudable dough. The dough was extruded through an 1.0mm screen using a twin screw extruder (Luwa model EXDS-60). The extrudate was spheronized on a Luwa Marumerizer (model QY-400) using a 2mm friction plate at 500 rpm and dried in a fluidized bed at 40° C. The microparticles contained 5.6% Eudragit E100 polymer and 94.4% ibuprofen.

Control Microparticles

A second formulation was made using a neutral binder. 900 grams of ibuprofen were mixed with 270 grams of Avicel RC 581 binder and 560 ml of water. The resulting dough was extruded and spheronized as above. Dissolutions were performed on 200 mg samples of both microparticles using USP Method I (Basket) at 50 rpm. USP buffers at pH 5.5, 6.2, 6.8, and 7.5 were used as dissolution media. Table I compares the dissolution profiles for the microparticles formed using the conventional Avicel RC 581 binder to the results using the pH controlled membrane of this invention. For the conventional microparticles the dissolution rate increased greatly with increasing pH, whereas for the microparticles with the pH controlled Matrix, the dissolution rate actually decreased with increasing pH.

TABLE I

Effect of pH on the Dissolution Rate Ibuprofen Microparticles

| Time (hrs) | Percent Dissolved | | | |
|---|---|---|---|---|
| | pH 5.5 | pH 6.2 | pH 6.8 | pH 7.5 |
| Conventional Microparticles: | | | | |
| 0.5 | 15.4 | 35.7 | 65.7 | 83.1 |
| 1 | 29.8 | 56.4 | 88.0 | 98.5 |
| 2 | 41.4 | 77.9 | 100 | 100 |
| 3 | 51.9 | 90.5 | 100 | 100 |
| 4 | 60.0 | 98.6 | 100 | 100 |
| 6 | 72.6 | 100 | 100 | 100 |
| Microparticles with pH Controlled Matrix: | | | | |
| 0.5 | 73.6 | 72.9 | 47.6 | 19.7 |
| 1 | 81.8 | 85.2 | 64.6 | 29.4 |
| 2 | 91.1 | 94.8 | 80.2 | 42.2 |
| 3 | 96.1 | 98.0 | 86.3 | 52.8 |
| 4 | 97.8 | 98.9 | 92.1 | 61.4 |
| 6 | 99.6 | 100 | 97.9 | 74.0 |

EXAMPLE II

Ibuprofen Microparticles Coated with a Neutral Diffusion Barrier

Both batches of microparticles made in Example I were coated with a neutral diffusion membrane to provide sustained release of the drug. Eudragit NE30D was applied to the microparticles by the Wurster process. The weight of the applied coat was 3% of the final weight of the coated microparticle. Dissolutions were performed as in Example I to determine the release rates and the pH dependencies of the two formulations. Table II dramatically illustrates that the conventional coated ibuprofen microparticles have a release rate that is very highly dependent on pH while the coated microparticles of the present invention provide a release rate that is essentially constant over the intestinal pH range.

TABLE II

Effect of pH on the Dissolution Rate Ibuprofen Microparticles

| Time (hrs) | Percent Dissolved | | | |
|---|---|---|---|---|
| | pH 5.5 | pH 6.2 | pH 6.8 | pH 7.5 |
| Conventional Microparticles with 3% Eudragit NE30D Coat: | | | | |
| 0.5 | 7.1 | 16.2 | 36.1 | 47.3 |
| 1 | 10.5 | 25.6 | 58.0 | 70.8 |
| 2 | 17.7 | 43.0 | 84.0 | 95.1 |
| 3 | 27.5 | 60.8 | 95.0 | 98.8 |
| 4 | 34.7 | 72.9 | 98.4 | 99.6 |
| 6 | 45.6 | 87.3 | 99.5 | 100 |
| pH Controlled Matrix Microparticles with 3% Eudragit NE30D Coat: | | | | |
| 0.5 | 5.6 | 4.5 | 5.8 | 7.3 |
| 1 | 9.0 | 7.3 | 10.2 | 11.3 |
| 2 | 16.2 | 10.4 | 16.7 | 23.6 |
| 3 | 19.5 | 13.1 | 22.0 | 27.9 |
| 4 | 22.5 | 16.2 | 26.6 | 35.3 |
| 6 | 27.3 | 20.8 | 35.3 | 47.6 |

EXAMPLE III

Gemfibrozil Microparticles

The carboxylic acid group of gemfibrozil has pKa of 4.7. Since the rest of the molecule is hydrophobic, the solubility of the drug increases greatly with increasing pH over the intestinal pH range. The drug was mixed with Eudragit E100 and extruded to form microparticles with a membrane that impedes dissolution more at higher pH than at lower pH. 162 grams of E100 were dissolved in a solution of 50 grams concentrated HCl in 450 ml of water. The polymer solution and drug were thoroughly mixed to form an extrudable dough. The dough was extruded through a 1.0 mm screen, spheronized, and dried as in Example I.

Dissolutions were performed on 80 mg samples of the microparticles using the dissolution procedure in Example I. Table III shows the dissolution profiles for the microparticles formed using the pH controlled membrane of this invention. The dissolution rate actually decreases with increasing pH.

TABLE III

Effect of pH on the Dissolution Rate Gemfibrozil Microparticles with pH Controlled Membrane

| Time (hrs) | Percent Dissolved | | | |
|---|---|---|---|---|
| | pH 5.5 | pH 6.2 | pH 6.8 | pH 7.5 |
| 0.5 | 62.8 | 66.2 | 14.7 | 10.2 |
| 1 | 70.8 | 74.9 | 21.7 | 15.4 |
| 2 | 74.5 | 83.1 | 34.6 | 23.2 |
| 3 | 76.3 | 87.1 | 45.6 | 30.4 |
| 4 | 77.7 | 90.9 | 54.3 | 37.9 |
| 6 | 80.6 | 94.3 | 65.9 | 49.9 |

EXAMPLE IV

Gemfibrozil Microparticles with a pH Controlled Matrix and A Neutral Diffusion Barrier Coat The microparticles produced in Example III were coated with a neutral diffusion barrier to provide a more sustained-release of the drug. A coating formulation for applying a neutral diffusion membrane was made by mixing 75 grams Eudragit NE30D, 16.9 grams PVP K30, 9.4 grams magnesium stearate, and 142.5 grams water. 82.9 grams of this formulation was applied to 315 grams of the Example IV microparticles by the Wurster process. The weight of the applied coat was 5% of the final weight of the coated microparticle.

Conventional microparticles were formed by mixing 800 grams gemfibrozil and 200 grams Avicel RC-581 were mixed with enough water to form an extrudable dough. The resulting dough was extruded through a 0.5 mm screen, spheronized, and dried as in Example I. The resulting microparticles were coated with Eudragit NE30D by the Wurster process to form a neutral diffusion membrane. The weight of the coat was 16% of the weight of the coated microparticle.

Dissolutions were performed on 80mg samples of both formulations as described in Example I. Table IV shows that application of the neutral diffusion membrane caused the microparticle with a pH controlled material to have a release rate that increased with increasing pH. However, the microparticle with the conventional membrane had a worse increase in dissolution rate as the pH increased.

TABLE IV

Effect of pH on the Dissolution Rate of Gemfibrozil Microparticles Coated with a Neutral Diffusion Membrane

| Time (hrs) | Percent Dissolved | | | |
|---|---|---|---|---|
| | pH 5.5 | pH 6.2 | pH 6.8 | pH 7.5 |
| Conventional Microparticles with a Neutral Diffusion Membrane: | | | | |
| 1 | 1.2 | 4.0 | 10.3 | 23.1 |
| 2 | 2.8 | 7.6 | 20.6 | 46.1 |
| 3 | 4.0 | 11.0 | 30.5 | 65.6 |
| 4 | 5.5 | 14.4 | 40.0 | 79.5 |
| 6 | 9.0 | 21.1 | 57.7 | 100 |
| Microparticles with pH Controlled Matrix and Neutral Diffusion Membrane: | | | | |
| 1 | 6.2 | 4.5 | 4.2 | 15.1 |
| 2 | 9.0 | 8.5 | 12.6 | 29.0 |
| 3 | 12.5 | 12.5 | 20.7 | 42.1 |
| 4 | 15.8 | 16.6 | 29.0 | 52.3 |
| 6 | 20.3 | 22.7 | 41.7 | 69.2 |

EXAMPLE V

Gemfibrozil Microparticles with a pH Controlled Material and a pH Controlled Diffusion Membrane The gemfibrozil microparticles were made as described in Example III except an 0.5mm screen was used. These microparticles were coated with a pH controlled diffusion membrane to provide sustained release and to further reduce the pH dependency of the release rate.

A pH controlled coating formulation was made by mixing 100 grams of Eudragit NE30D and 15 grams magnesium stearate with an Eudragit E100 solution prepared by dissolving 60 grams of Eudragit E100 in a solution of 20 grams concentrated HCl in 435 ml water. 555 grams of this mixture was applied to 1000 grams of the microparticles by the Wurster process. To prevent the disintegration of this pH controlled diffusion membrane at low pH, an additional protective coating was applied to the resulting Product. 190 grams NE30D, 14.4 grams PVP K30, 14.4 grams magnesium stearate, and 210 grams water were mixed to produce the protective coating formulation. The Wurster process was used to apply 350 grams of this formulation to 1100 grams of the above product.

Dissolutions were performed as described in Example I on 80 mg samples of the resulting product. The results of the dissolution are shown in Table V. The dramatic reduction in the dependency of the dissolution rate on the pH is especially evident when the sustained release gemfibrozil formulation of this example is compared to the formulation prepared in Example IV. The significant improvement in this example is attributed to use of the pH controlled material and diffusion membrane working in concert together. Conversely, Example IV uses a conventional membrane and diffusion barrier.

TABLE V

Effect of pH on the Dissolution Rate of Gemfibrozil Microparticles Coated with a Neutral Diffusion Membrane

| Time (hrs) | Percent Dissolved | | | |
|---|---|---|---|---|
| | pH 5.5 | pH 6.2 | pH 6.8 | pH 7.5 |
| Conventional Microparticles with a Neutral Diffusion Membrane: | | | | |
| 1 | 1.2 | 4.0 | 10.3 | 23.1 |
| 2 | 2.8 | 7.6 | 20.6 | 46.1 |
| 3 | 4.0 | 11.0 | 30.5 | 65.6 |
| 4 | 5.5 | 14.4 | 40.0 | 79.5 |
| 6 | 9.0 | 21.1 | 57.7 | 100 |
| Microparticles with pH Controlled Matrix and a pH Controlled Diffusion Membrane: | | | | |
| 1 | 15.6 | 13.1 | 9.7 | 13.5 |
| 2 | 21.5 | 20.3 | 18.0 | 27.1 |
| 3 | 29.3 | 27.1 | 26.5 | 40.4 |
| 4 | 32.7 | 33.0 | 34.0 | 51.8 |
| 6 | 37.6 | 44.7 | 48.8 | 72.3 |

EXAMPLE VI

PH Independent Delayed Sustained Release Microparticles

An enteric coat was applied to the coated microparticles of Example V to produce a pH independent delayed sustained release gemfibrozil formulation.

60 grams of Coateric YPA-6-2366 was dispersed in 237.6 grams water and 2.4 grams of 30% ammonium hydroxide was added. The Wurster process was used to spray 154 grams of this mixture onto 354 grams of the coated microparticles of Example V. Dissolutions were performed on 80 mg samples using the USP basket method at 50 rpm. The dissolutions were performed in 0.1N HCl for 2 hours. After 2 hours the 0.1 N HCl was replaced with a pH 5.5, 6.2, 6.8 or 7.5 buffer. The dissolution results in Table VI shows that delayed sustained release of gemfibrozil with greatly reduced pH dependencies over the intestinal pH range was achieved.

TABLE VI

Effect of pH on the Dissolution Rate of enteric coated Gemfibrozil Microparticles with pH Controlled Membrane and Diffusion Membrane

| Time (hrs) | Percent Dissolved | | | |
|---|---|---|---|---|
| | 0.1 N HCl | | | |
| 2 | 0 | 0 | 0 | |
| | pH 6.2 | pH 6.8 | pH 7.5 | |
| 3 | 3.5 | 10.1 | 11.1 | |
| 4 | 8.9 | 15.9 | 21.5 | |
| 6 | 15.3 | 24.8 | 42.0 | |

In yet another embodiment of the present invention, a sustained-release pH independent pharmaceutical preparation preferably contains a granular drug having a solubility that decreases with increasing pH. For example, dipyridamole has amine groups which are protonated at low pH causing the drug to be readily soluble, whereas at high pH the amine groups are in the neutral form and thus, the drug is sparingly soluble. Other drugs which have a solubility that decreases with increasing pH include verapamil.

Consequently for this sustained-release pH independent pharmaceutical preparation, the granular drug such as dipyridamole is used with a pH controlled material having a permeability which increases with increasing pH. In this regard, polymers that form diffusion barriers or membranes with permeabilities that increase with increasing pH have been produced. More specifically, applicants' copending patent application Ser. No. 354,105, filed May 22, 1989 now U.S. Pat. No. 4,983,401, issued Jan. 28, 1991, illustrates a film forming polymer containing a moiety that is hydrophobic at low pH and hydrophilic at high pH. Further, the pH range and the amount of change in permeability of the diffusion barrier or membrane can be designed by selection of the type and concentration of the pH controlled moiety in the polymer. Polymers that can be used for as the pH controlled material in this embodiment includes cellulose acetate phthalate (CAP) which has been modified to render it insoluble at intestinal pH, or an insoluble diffusion barrier such as a methacylic/acrylic acid ester copolymer (MAA) which has been modified to render it pH sensitive. In addition to these polymers, cellulose acetate trimellitate, hydroxyethyl cellulose phthalate, cellulose acetate tetrahydrophthalate, hydroxypropylmethyl cellulose phthalate and polyvinyl acetate phthalate may be modified by attachment of hydrophobic side chains such as long chain fatty acids so that they form films with low permeability in acidic environments but remain intact by have higher permeability at alkaline or neutral pH. Alternatively, enteric polymers may be admixed with polymers that form neutral diffusion membranes to form matrices or diffusion membrane coatings with permeabilities that increase with increasing pH. The pH controlled material should be in a ratio with the granular drug such that the resulting preparation has a drug release rate that is independent from pH.

Additionally, enteric polymers may be admixed with the aforementioned polymers to form pH controlled materials having permeabilities that increase with increasing pH. The pH controlled material is preferably used in the same manner as the aforementioned pH controlled material for drugs having a solubility that increases with increasing pH. Likewise, a diffusion membrane may be used in this embodiment as well. In addition to or in place of the diffusion membrane, an enteric coat may be applied to the coated or uncoated microparticles of the present invention in order to protect the formulation from gastric fluids and/or to provide a delayed release of drug. In this regard, reference is made to copending patent application Ser. No. 017,988, filed Feb. 24, 1987 which is hereby incorporated by reference. A delayed sustained-release of drug beyond the gastric emptying time may be accomplished by using an acid to maintain the enteric coat in the impermeable state, as shown in copending patent application Ser. No. 332,154, filed Apr. 3, 1989 now U.S. Pat. No. 5,026,559, issued June 25, 1991, which is also hereby incorporated by reference.

Having thus described the present invention in detail, it will be obvious to those skilled in the art that various changes or modifications may be made without departing from the scope of the invention defined in the appended claims and described in the specification.

What is claimed is:

1. A sustained-release pH independent pharmaceutical preparation having multi-units of microparticles having a particle size of from about 100 to 2,000 microns comprising:
   a) a granular drug which is less soluble at low pH and more soluble at high pH and
   b) a membrane or matrix of pH controlled material as a diffusion barrier for said drug, said pH controlled material being formed from at least one polymer selected from the group consisting of acrylics, polyacrylates, polymethacrylates, polyvinyls, and cellulosics, which polymer has tertiary amine side chains such that said polymer is hydrophilic at low pH and hydrophobic at higher pH, and said pH controlled material being in a ratio to said granular drug of less than 1:2 but greater than 1:50 such that the resulting sustained-release pharmaceutical preparation is independent from the pH environment in that the permeability of said diffusion barrier decreases with increasing pH while the solubility of said drug increases with increasing pH.

2. The sustained-release pH independent pharmaceutical preparation of claim 1 wherein said drug is selected from the group consisting of ibuprofen, genfibrozil, indomethacin, sulindac naproxen, tolmetin, fenoprofen and furosemide.

3. A sustained-release pH independent pharmaceutical preparation comprising multi-units of microparticles having a particle size of from about 100 to 2,000 microns comprising:
   a) a granular drug which is more soluble at low pH and less soluble at high pH; and
   b) a membrane or matrix of pH controlled material as a diffusion barrier for said drug, said pH controlled material being formed from at least one polymer selected from the group consisting of cellulose acetate phthalate, methacrylic/acrylic acid copolymer, cellulose acetate trimellitate, hydroxypropylmethyl cellulose phthalate, polyvinyl acetate phthalate, hydroxyethyl cellulose phthalate and cellulose acetate tetrahydrophthalate, which polymer has long chain fatty acid side chains such that said polymer is hydrophobic at low pH and hydrophilic at higher pH, and said membrane being in a ratio to said granular drug of less than 1:2 but greater than 1:50 such that the resulting sustained-release pharmaceutical preparation is independent from the pH environment in that the permeability of said diffusion barrier increases with increasing pH while the solubility of said drug decreases with increasing pH.

4. The sustained-release pH independent pharmaceutical preparation of claim 1 wherein said pH controlled material is a layer of said polymer surrounding said granular drug.

5. The sustained-release pH independent pharmaceutical preparation of claim 4 further including as a diffusion membrane a layer of a pH neutral polymer over said pH controlled material layer.

6. The sustained-release pH independent pharmaceutical preparation of claim 5 wherein said pH neutral polymer is an acrylic resin.

7. The sustained-release pH independent pharmaceutical preparation of claim 1 wherein said PH controlled material is admixed into a diffusion membrane.

8. The sustained-release pH independent pharmaceutical preparation of claim 7 wherein said admixed pH controlled material and diffusion membrane is formed as a layer on said granular drug by a spray coating process.

9. The sustained-release pH independent pharmaceutical preparation of claim 1 wherein pH controlled material is in the form of a matrix into which said granular drug is admixed so as to form a spheroidal core.

10. The sustained-release pH independent pharmaceutical preparation of claim 1 further including a diffusion membrane in the form of a layer of pH neutral polymer surrounding said spherical core.

11. The sustained-release pH independent pharmaceutical preparation of claim 10 wherein said drug is ibuprofen.

12. The sustained-release pH independent pharmaceutical preparation of claim 10 wherein said drug is gemfibrozil.

13. A sustained-release pH independent pharmaceutical preparation comprising multi-units of microparticles comprising:
 a) a granular drug containing a drug which is more soluble at low pH and less soluble at high pH; and
 b) a pH controlled diffusion material, said pH controlled material being formed from at least one polymer that is hydrophobic at low pH and hydrophilic at higher pH, and said membrane being in a ratio with said granular drug such that the resulting sustained-release pharmaceutical preparation is independent from the pH environment.

14. The sustained-release pH independent pharmaceutical preparation of claim 13 wherein said drug is selected from the group consisting of dipyridamole, verapamil, chlorpheniramine, pseudoephedrine, quinidine, and clonidine.

15. The sustained-release pH independent pharmaceutical preparation of claim 13 further including as diffusion membrane a layer of pH neutral polymer.

16. The sustained-release pH independent pharmaceutical preparation of claim 13 which further includes an outer sheath of enteric polymer to provide a delayed release of said drug.

* * * * *

UNITED STATES PATENT AND TRADEMARK OFFICE
CERTIFICATE OF CORRECTION

PATENT NO. : 5,102,668
DATED : April 7, 1992
INVENTOR(S) : Herman J. Eichel and Brent D. Massmann It is certified that error appears in the above-identified patent and that said Letters Patent is hereby corrected as shown below:

The following (original claim 5) should appear as claim 3:

3. The sustained-release pH independent pharmaceutical preparation of claim 1 wherein said ratio of pH controlled material to said granular drug is 1:19.

Claim 3 should be "claim 13" and claim 13 as shown in the patent should be deleted Signed and Sealed this Twentieth Day of July, 1993

Attest:

MICHAEL K. KIRK

*Attesting Officer*     *Acting Commissioner of Patents and Trademarks*